(12) United States Patent
Ueno et al.

(10) Patent No.: US 7,169,523 B2
(45) Date of Patent: Jan. 30, 2007

(54) CHARGE CONTROLLERS

(75) Inventors: Ryuzo Ueno, Nishinomiya (JP); Masaya Kitayama, Takarazuka (JP); Kenji Minami, Sennan (JP); Hiroyuki Wakamori, Sannan-cho (JP); Nobuhiro Yonetani, Nishinomiya (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 10/511,097

(22) PCT Filed: Apr. 18, 2003

(86) PCT No.: PCT/JP03/04961

§ 371 (c)(1),
(2), (4) Date: Oct. 14, 2004

(87) PCT Pub. No.: WO03/091808

PCT Pub. Date: Nov. 6, 2003

(65) Prior Publication Data

US 2005/0147909 A1  Jul. 7, 2005

(30) Foreign Application Priority Data

Apr. 26, 2002  (JP) ............................. 2002-126540

(51) Int. Cl.
*G03G 9/097* (2006.01)
(52) U.S. Cl. .............................. 430/108.2; 430/108.4; 430/108.21
(58) Field of Classification Search ............ 430/108.2, 430/108.4, 108.21; 558/488; 568/735
See application file for complete search history.

(56) References Cited

U.S. PATENT DOCUMENTS 5,786,523 A * 7/1998 Ueno et al. ................. 568/735

6,409,812 B1 * 6/2002 Ueno et al. ............... 106/31.51

FOREIGN PATENT DOCUMENTS

| JP | 10-333361 A | 12/1998 |
|---|---|---|
| WO | WO 96/32366 A1 | 10/1996 |
| WO | WO 00/23526 A1 | 4/2000 |

* cited by examiner

*Primary Examiner*—Mark A. Chapman
(74) *Attorney, Agent, or Firm*—Sughrue Mion, PLLC (57) ABSTRACT

The present invention provides a safe charge control agent which exhibits an excellent negative chargeability and excellent dispersibility in and compatibility with binder resins, and is even applicable for col or toners. Specifically, the charge control agent consists of a naphthol derivative of formula [I]:

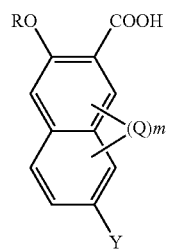

and a salt thereof, and an electrophotographic toner comprising the agent are provided.

4 Claims, 7 Drawing Sheets

CHARGE CONTROLLERS

TECHNICAL FIELD

The present invention relates to a charge control agent consisting of a naphthol derivative. The present invention also relates to electrophotographic toner comprising said charge control agent.

BACKGROUND ART

Developers used in electrophotographic systems such as copying machine include two-component developer, which comprises carrier and toner, and single component developer, which is free of carrier. Conventional toners used in both types of developers consist of fine particles of binder resin in which colorants, such as pigment and dye, are dispersed.

One of the important properties of the toner is triboelectric chargeability. That is, properties required for toners include that they can generate a suitable amount of positive or negative electrostatic charge upon contacting with a carrier or a charge providing device, and that the amount of the charge is stable over continuous use or under an adverse environment. Binder resin, the main component of the toner, may be triboelectrically chargeable but the amount of the generated electrostatic charge is not sufficient, and therefore image fogging may occur to make the resulting image unclear. In order to impart further triboelectric charging property, toners in general are added with a charge control agent so that the electrostatic charge is controlled suitably.

Generally known and used charge control agent for electrophotographic toners include positively chargeable agents such as nigrosin dyes and quaternary ammonium salts, and negatively chargeable agents such as metal containing monoazo dyes, metal-salicylic acid complexes and copper phthalocyanine pigments.

DISCLOSURE OF THE INVENTION

Problems to be Solved by the Invention

Those known charge control agents, especially negatively chargeable charge control agents, comprise pigments or dyes as their main component and may be a strong colorant. Accordingly, they are not suitable for color toners in spite of their excellent chargeability.

In addition, metal complex charge control agents have poor dispersibility in and compatibility with the resin and may cause inhomogeneous charge of the resulting toner. Further, the agent may easily be released from the toner particles and stain on the development sleeve or carriers, or lower the chargeability over continuous copying. Said problems may cause reduction of resulting image density.

Further, the complex structure of a metal containing compound like metal complex invites high manufacturing cost. Metals like chrome may affect negatively on human body and environment. There has been a demand for developing a metal free charge control agent.

In order to dissolve the above problems, an object of the present invention is to provide a novel charge control agent having an excellent dispersibility in and compatibility with binder resins and is suitable for manufacturing color toners, and is safe for human body as well as environment.

Further object of the present invention is to provide electrophotographic toner of which particles can be charged uniformly within a short time period and the triboelectric charging property is stable over time. Said toner can provide high quality images with high image density and less fogging.

Solution of the Problems

The present inventors have successfully synthesized novel naphthol derivatives using 2-hydroxynaphthalene-3,6-dicarboxylic acid as a starting compound, studied their physical properties and found that the derivatives have an excellent negatively charging property and are useful as charge control agent for electrophotographic toners.

Accordingly, the present invention provides a charge control agent consisting of a compound represented by formula [I]

[I]

wherein Y is selected from the group consisting of an esterified carboxyl group and a group of —(CONH)n-X (wherein X is selected from the group consisting of an optionally branched and optionally substituted hydrocarbon group which may have an unsaturated bond, an optionally substituted aromatic group and a heterocyclic group having conjugated double bonds, n is an integer of 1 or 2);

R is selected from the group consisting of hydrogen atom, alkaline metal, an optionally branched, optionally substituted C1 to C6 alkyl and acyl groups, and phenylalkyl group;

Q is selected from the group consisting of an optionally branched C1 to C6 alkyl and alkoxy groups, halogen atom, nitro group, nitroso group, amino group and sulfo group; and m is an integer of 0 to 3 or a salt thereof.

In the above formula, esterified carboxyl group of Y may include a C1 to C6 alkoxycarbonyl group, such as methoxycarbonyl, ethoxycarbonyl, propyloxycarbonyl, isopropyloxycarbonyl, butoxycarbonyl, pentyloxycarbonyl and hexyloxycarbonyl; phenoxycarbonyl group and phenacyloxycarbonyl group. In case the group has an aromatic moiety, said moiety may have a substituent.

The group X may be an optionally branched and optionally substituted hydrocarbon group which may have an unsaturated bond, preferably a C1 to C20 alkyl group such as methyl, ethyl, propyl, butyl, pentyl, hexyl, decyl, dodecyl, lauryl and stearyl; a C2 to C6 alkenyl group such as vinyl, allyl, propylenyl, butylenyl, pentylenyl and hexylenyl; an optionally substituted aromatic group such as, phenyl, naphthyl, anthryl, anthraquinonyl and pyrenyl; and an optionally substituted heterocyclic group having conjugated double bonds such as benzimidazolonyl, carbazolyl, pyridyl, thiazolyl, benzothiazolyl, imidazolyl, indryl, thiofuryl, phenothiazinyl, acridinyl and quinolinyl.

Examples of substituents in each definition wherein the group is optionally substituted, may include a halogen atom, a halogenated lower alkyl group, nitro group, a lower alkyl group, a lower alkoxy group such as methoxy, cyano group, phenyl group, naphthyl group, phenoxy group, furyl group, amino group, triazinylamino group, pyrimidylamino group, pyridazinylamino group, pyridylamino group, benzoylamino group, sulfo group, hydroxy group, an esterified carboxyl group such as alkoxycarbonyl and phenoxycarbonyl, an amidized carboxyl group such as phenylaminocarbonyl, alkylaminosulfonyl group and a C2 to C6 alkenyl group which may have an aryl group.

When the substituent contains an aromatic ring, the compound may further have one or more substituents such as a halogen atom, a lower alkyl, a lower alkoxy, phenyl and cyano groups on said aromatic ring.

In the present specification and "lower" represents a group having 1–6 carbon atoms.

"Aromatic group" represents a 6-membered monocyclic aromatic group or condensed ring group consisting of up to 4 aromatic rings.

"Heterocyclic group having conjugated double bonds" represents a 5- or 6- membered mono-cyclic group or condensed ring group having at least one hetero-atom selected from N, S and O and conjugated double bonds. When it represents a condensed ring group, said group may have up to 6 rings.

In the present invention, the naphthalene nuclei of the naphthalene derivative represented by formula [1] may optionally have a substituent of Q. The Q may be selected from the group consisting of an optionally branched C1 to C6 alkyl and alkoxy groups, halogen atom, nitro, nitroso, amino and sulfo groups.

The m, which represents the number of the substituents, is usually 0 and may be up to 3.

R is selected from the group consisting of hydrogen atom, an alkaline metal, optionally branched and optionally substituted C1 to C6 alkyl and acyl groups and a phenylalkyl group. Examples of the substituents for R may include a halogen atom, a lower alkyl, a lower alkoxy, amino, cyano, nitro, and nitroso groups.

According to the present invention, the salt of naphthol derivative represented by formula [I]is not specifically limited and may preferably be alkaline metal salt such as sodium or potassium salt.

The charging amount of naphthol derivative of the present invention was measured by means of the blow-off charge amount measurement method under the condition described below. The derivative was negatively charged and the absolute value of the charging amount was equal to or more than 10.0 μC/g, preferably 50.0 μC/g.

According to the present invention, the naphthol derivative of formula [I] wherein Y is —(CONH)n-X, wherein n is 1, and X is C8 to C18 alkyl group is preferable. Among them, the compounds shown below are especially preferable.

(1)

(2)

(3)

The above described naphthol derivatives can be prepared by the following procedure.

Firstly, 2-hydroxynaphthalene-3,6-dicarboxylic acid is obtained by means of the method described in WO98/17621 or Japanese Patent Application Laid Open Hei 10-519205, i.e. by reacting potassium 2-naphtholate and carbon dioxide, aciding out the reaction product and then optionally purifying the product.

Then, the obtained 2-hydroxynaphthalene-3,6-dicarboxylic acid is reacted with methyl iodide in a solvent such as N,N-dimethylformamide to give 3-methylester of 2-hydroxynaphthalene-3,6-dicarboxylic acid.

Thus obtained ester is reacted with thionyl chloride or the like in a solvent such as xylene, sulfolane or tetrahydrofuran to give the corresponding acid chloride, and then the acid chloride is reacted with a predetermined alkylamine to give 3-methylester, 6-alkylamide of 2-hydroxynaphthalene-3,6-dicarboxylic acid.

The obtained product is then reacted with a base such as sodium hydroxide in an aqueous alcohol, the reaction is then neutralized with hydrochloric acid and the precipitate is collected by filtration, washed and dried to give the desired 6-alkylamide of 2-hydroxynaphthalene-3,6-dicarboxylic acid.

Toners for electrophotography comprising the charge control agent of the present invention are then illustrated below. The charge control agent of the present invention may preferably used for manufacturing either single component developer or two-component developer. In general, toners for electrophotography are prepared by dispersing additives such as colorant and charge control agent in the binder resin. The toner of the present invention may be manufactured in a manner similar to he conventional toners using the above described naphthol derivative as a charge control agent.

Examples of binder resins may include polystyrenes, acrylic polymers, styrene-acrylic copolymers, styrene-methacrylate copolymers, styrene-propylene copolymers, styrene-butadiene copolymers, styrene-maleic acid copolymers, polyolefins, polyesters, epoxy resins polyurethanes and polyvinyl butyrals. Those resins may be used alone or two or more of them may be used in combination.

Examples of the colorants may include carbon black, lamp black, iron black, cobalt blue, nigrosin dye, aniline blue, phthalocyanine blue, phthalocyanine green, hansa yellow, chrome yellow, rose bengal, triaryl methane dyes and monoazo and bisazo dyes or pigments. The colorants may be selected based on the desired color of the resulting toner.

The amount of the colorant per 100 parts by weight of the binder resin may be 1–20 parts and preferably 2–10 parts by weight.

The toner of the present invention comprises naphthol derivative of formula [I] as a charge control agent. The amount of the naphthol derivative per 100 parts by weight of the binder resin may be 0.1–10, and preferably, 0.0.1–5 parts by weight. In case the amount is less than 0.1 parts by weight, the derivative will not impart enough charge controlling effect, while in case where the amount is more than 10 parts by weight, the quality of the resulting toner may be deteriorated.

The electrophotographic toner of the present invention may comprise another known charge control agent such as metal containing monoazo dye, metal-salicylic acid complex and copper phthalocyanine pigment in combination with the naphthol derivative of formula [I].

In addition to the above, the toner of the present invention may comprises further additives such as low molecular weight olefine polymer and fine particle silica to improve fixing or flow property of the toner. The toner of the present invention may further comprise any additives used for conventional electrophotographic toners unless contrary to the object of the present invention.

The particle size of the toner is not particularly limited and preferably, equal to or less than 20 μm, more preferably, equal to or less than 10 μm.

The electrophotographic toner of the present invention may be manufactured by any known method. For example, but not limited to, the method wherein the above described ingredients are mixed uniformly by means of dry blender, Henschel mixer, ball mill or the like; the obtained mixture is melt and kneaded by means of a kneading machine such as Banbury mixer, heating roll, or single- or twin-axis extruder kneader; the uniformly kneaded matter is cooled and pulverized; and if desired, classified, and then added with the external additives to give the toner may be employed. Alternatively, any of known methods such as polymerizing method, microcapsule polymerizing method and spray dry method may be employed for the manufacture.

The charge control agent of the present invention exhibits good compatibility with resins and therefore, the agent can be admixed into the binder resin together with the other ingredients to give uniformly and stably chargeable toners. The charge control agent of the present invention may be fixed or embedded on the surface or the area adjacent to the surface of the fine particles comprising binder resin and a colorant by means of a known method using mechanical impact.

Advantageous Effects Over Prior Art

The charge control agent of the present invention exhibits high chargeability and an excellent compatibility with resins, which can be dispersed uniformly in the resin. The charge control agent is white to light-color which will not affect the color of the colorant.

The naphthol derivative of the present invention can be manufactured by means of a simple process with low cost.

The derivative will not affect badly on the human body as well as on the environment. In consequence, the property is suitable for charge control agent for electrophotographic toners, especially for negatively chargeable electrophotographic toners.

The electrophotographic toner of the present invention comprising the charge control agent of the present invention can be uniformly charged within a short time period and the triboelectric charging property is stable over time. Accordingly, by using the toner of the invention, high quality images with high image density and less fogging can be provided. Further, stain on the development sleeves and carriers with the charge control agent are effectively avoided and therefore, the toner can provide high density images stably over continuous copying. Further more, the charge control agent of the present invention has least impact on the color provided by the toner and therefore, useful for manufacturing color toners.

EXAMPLES

The present invention is further described in reference to the following examples. The following examples are intended only to illustrate the invention and are not to be construed to limit the scope of the invention.

Example 1

Figure 1:
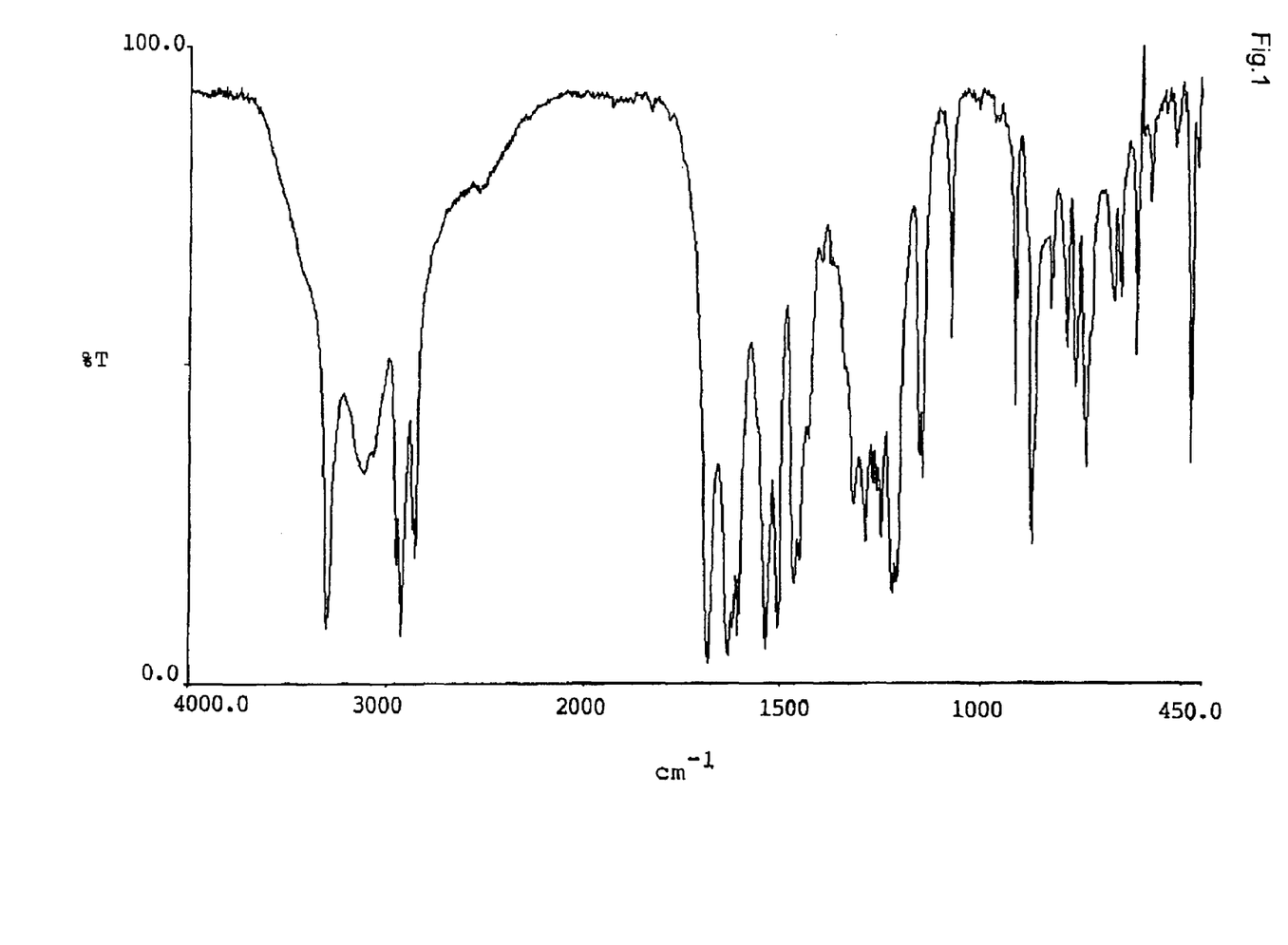
FIG. 1 is an infrared absorption spectrum (KBr) of the naphthol derivative obtained in Example 1.
Figure 2:
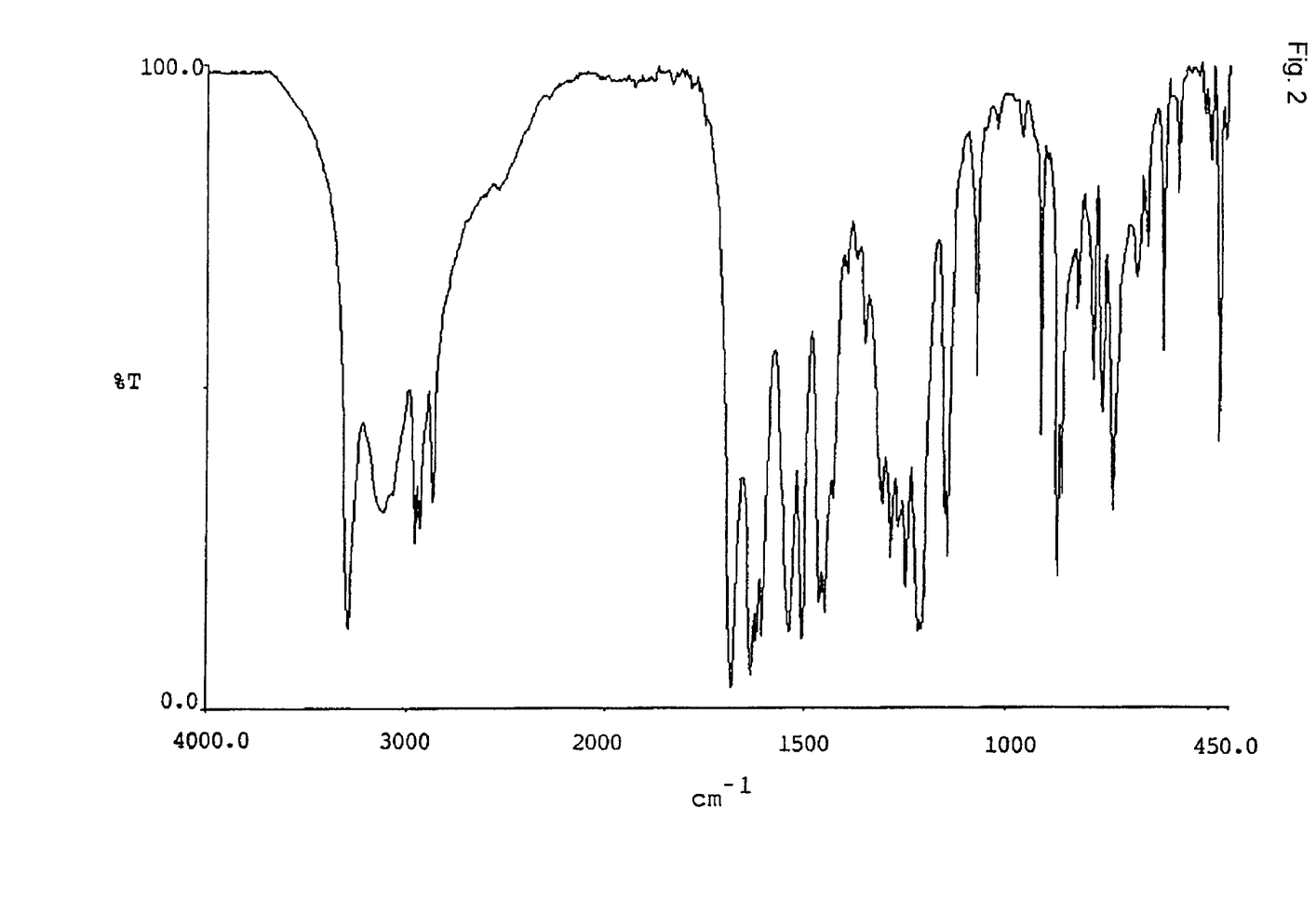
FIG. 2 is an infrared absorption spectrum (KBr) of the naphthol derivative obtained in Example 2.
Figure 3:
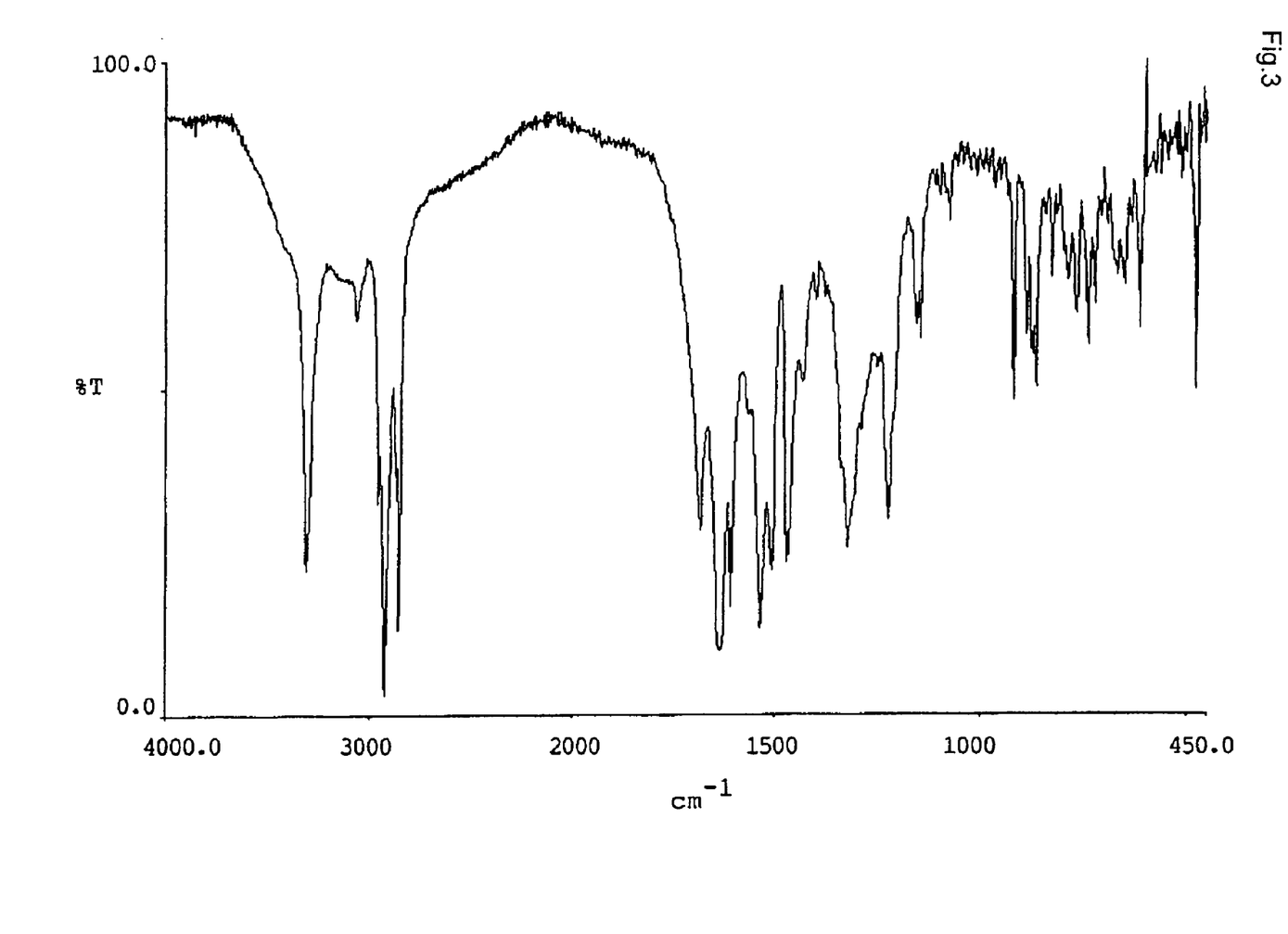
FIG. 3 is an infrared absorption spectrum (KBr) of the naphthol derivative obtained in Example 3.
Figure 4:
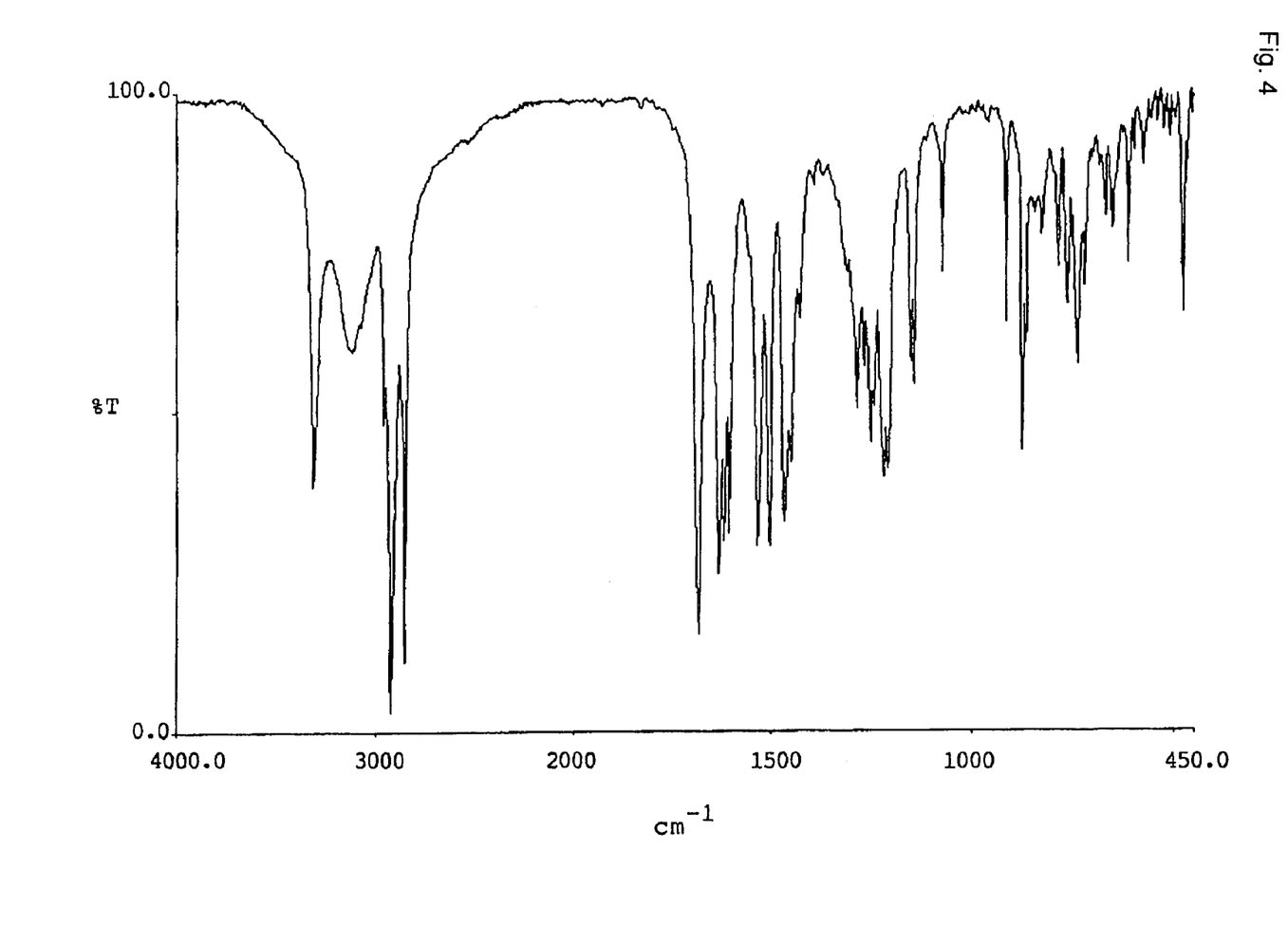
FIG. 4 is an infrared absorption spectrum (KBr) of the naphthol derivative obtained in Example 4.
Figure 5:
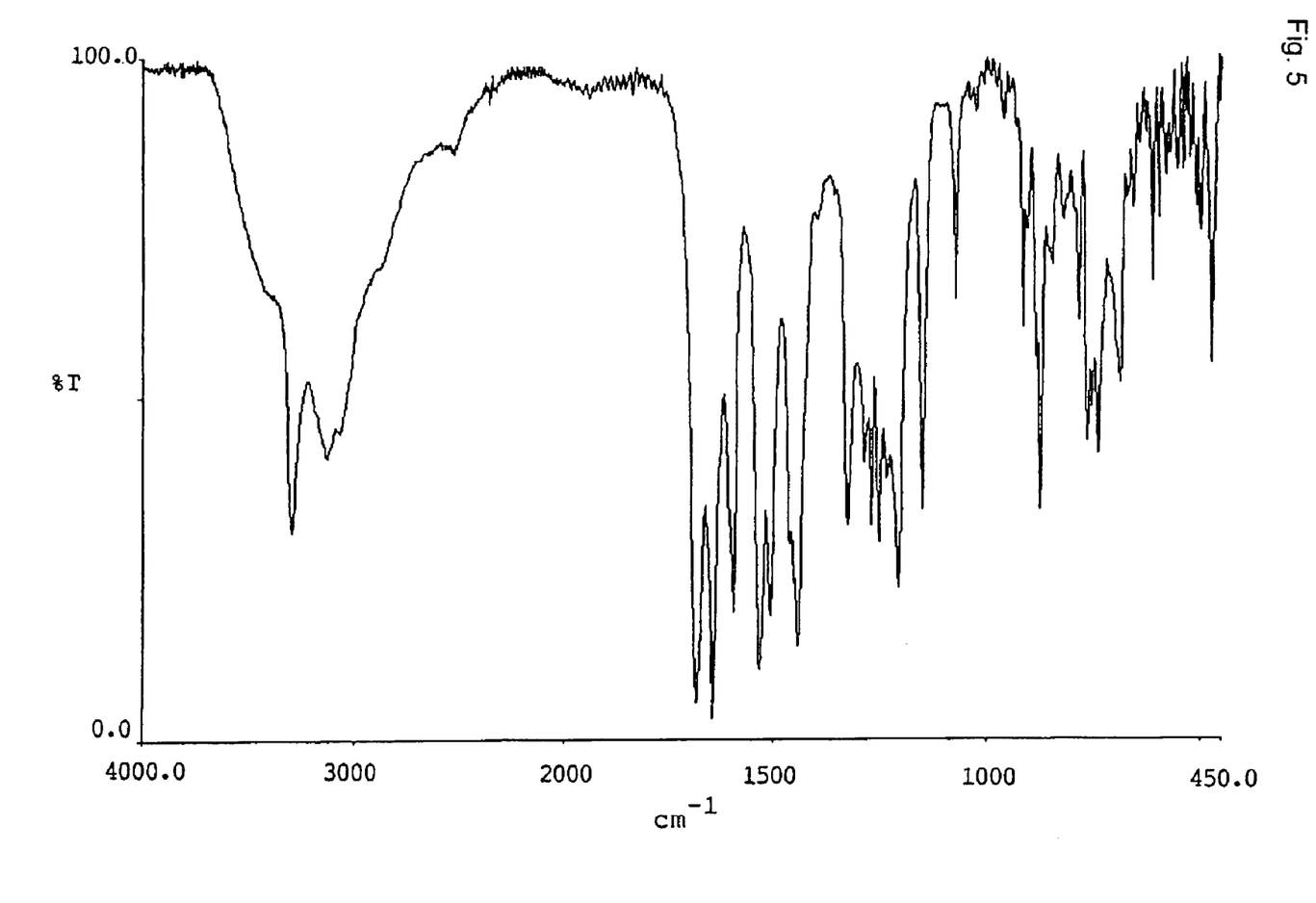
FIG. 5 is an infrared absorption spectrum (KBr) of the naphthol derivative obtained in Example 5.
Figure 6:
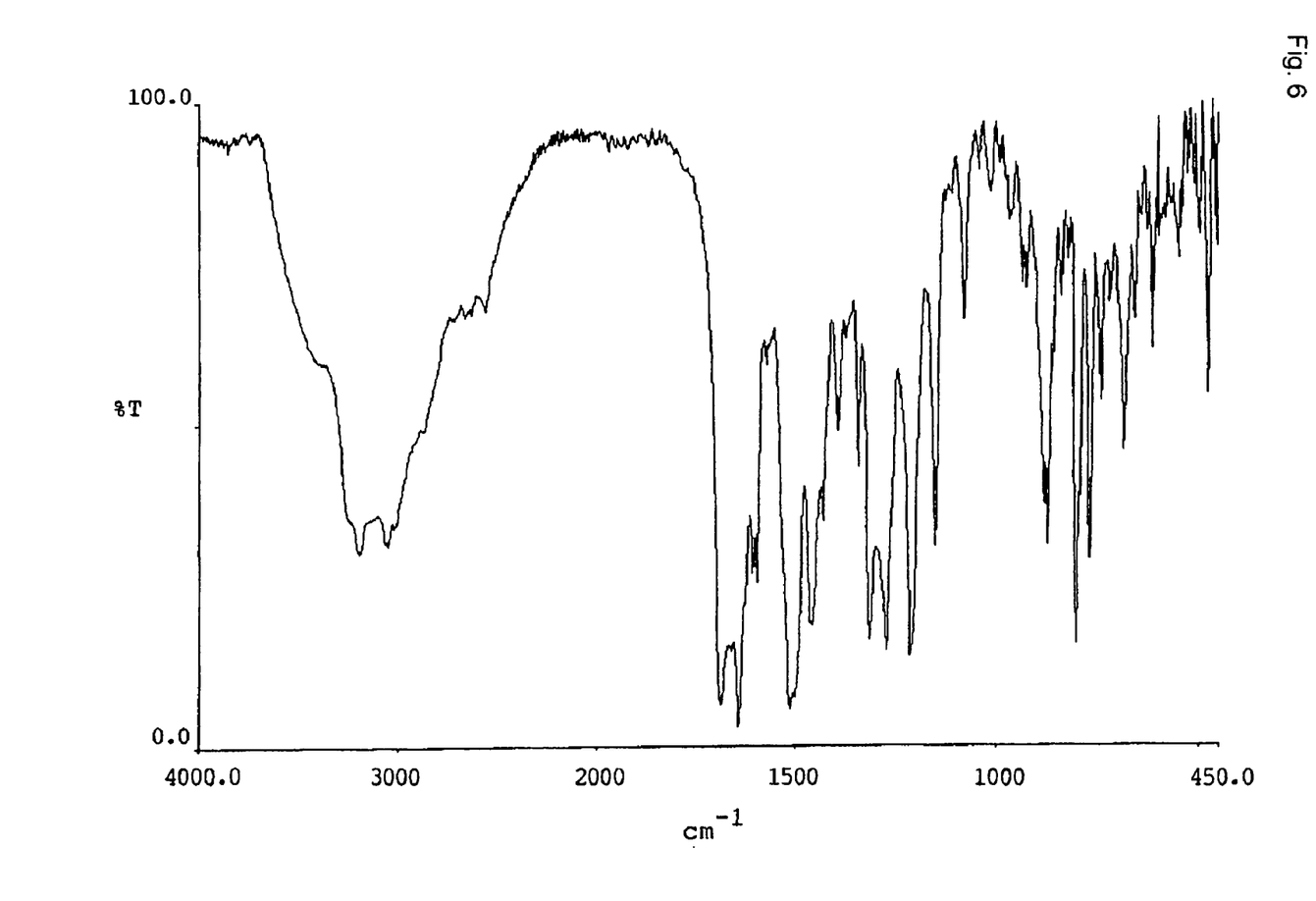
FIG. 6 is an infrared absorption spectrum (KBr) of the naphthol derivative obtained in Example 6.
Figure 7:
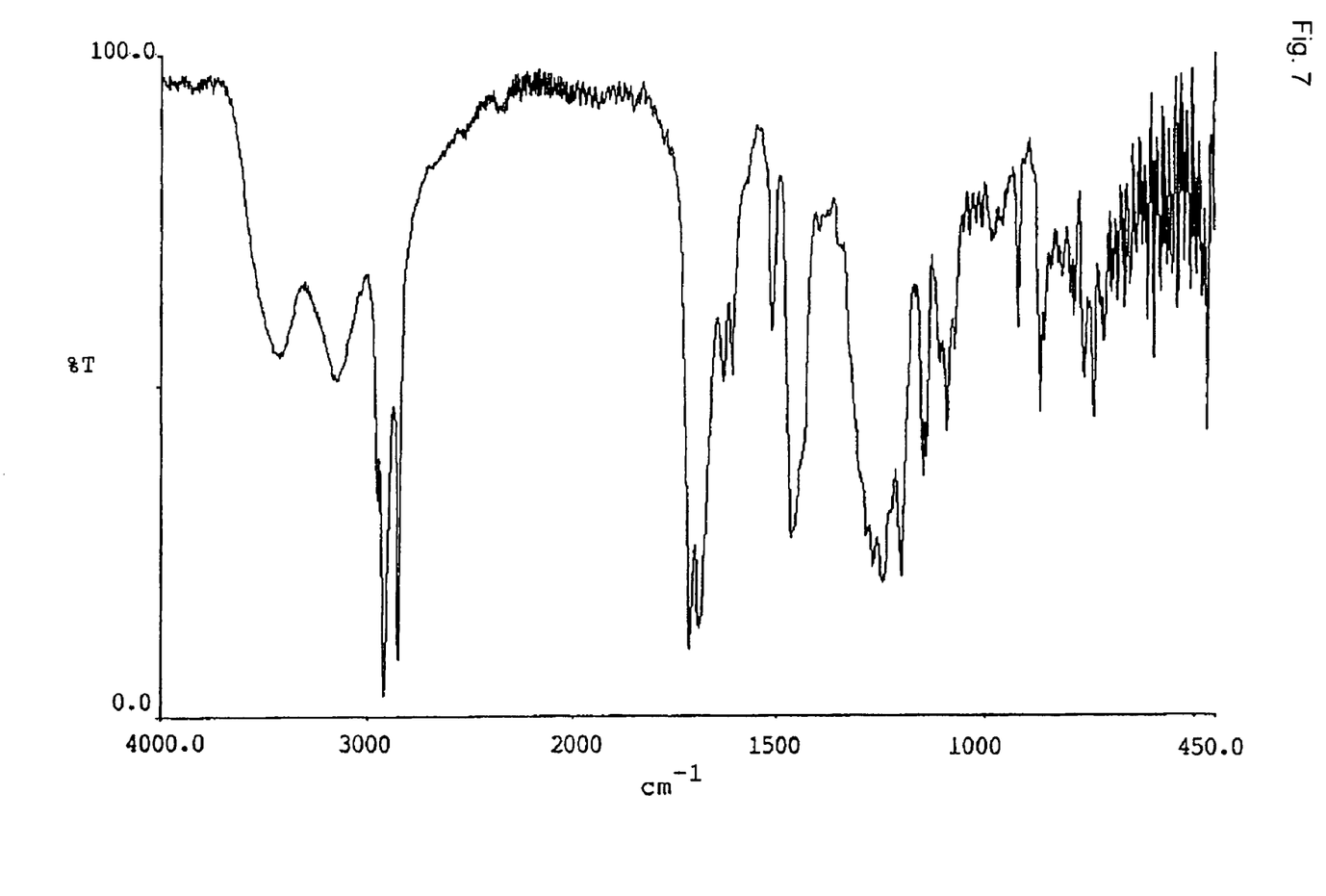
FIG. 7 is an infrared absorption spectrum (KBr) of the naphthol derivative obtained in Example 7.

2-hydroxy-3-hydroxycarbonyl-6-n-octylaminocarbonyl Naphthalene 2-hydroxy-6-hydroxycarbonyl-3-methoxycarbonyl naphthalene 17.3 g was dispersed in tetrahydrofuran 170 g, N,N-dimethylformamide was added thereto, and then, thionylchloride 12.5 g was added and the mixture was reacted at 50° C. for 2 hours. After that, the remaining thionyl chloride was distilled out together with the solvent. N-octylamine 18.4 g in tetrahydrofuran 170 g was added to the reaction and reacted under reflux for about 15 hours. After the reaction, the solvent was distilled out and then methanol 150 g was added to the reaction to give dispersion. The precipitates were collected by filtration and washed well with methanol and water. Thus obtained 2-hydroxy-3-metoxycarbonyl-6-n-octylaminocarbonyl naphthalene 15.2 g was dispersed in methanol 152 g, and sodium hydroxide 5.1 g in water 100 g was added thereto. The mixture was reacted for 2 hours at 70° C., treated with carbon, and the pH was adjusted to the range of 2–3 with hydrochloric acid. The precipitate was collected by filtration, washed well with water and dried to give the product 14.1 g as white powder (decomposition point: 304° C.). The infrared absorption spectrum (KBr) of the compound is shown in FIG. 1.

The triboelectric charging property of thus obtained 2-hydroxy-3-hydroxy carbonyl 6-n-octylaminocarbonyl naphthalene was determined by means of blow-off powder electrostatic charge tester (#TB200, Toshiba Chemical Corp, Tokyo, Japan) using metal mesh of 200-mesh (75 μm) under the condition shown below. The resulting triboelectric charge of said compound was −51.9 μC/g.

Measurement Conditions:
Temperature: 20° C.
Relative Humidity: 20%
Blow gas: $N_2$, 1.0Kg/cm2
Blow-off time: 60 seconds
Ferrite carrier was used.

Examples 2–7

Naphthol derivatives were prepared in the same manner as Example 1 except for using amine or alcohol listed in the table 1 instead of n-octylamine. The triboelectric charge and the decomposition point of the naphthol derivatives were determined. The results are shown in Table 1. The infrared absorption spectrums (KBr) of the respective compounds are shown in FIGS. 2–7.

TABLE 1

| Ex. | amine/alcohol | naphthol derivative | tribofrictional charge (μC/g) | decomposition temp. (° C.) |
|---|---|---|---|---|
| 2 | $n\text{-}C_4H_8NH_2$ | HO—, COOH, CONHC$_4$H$_9$ naphthalene | −15.3 | 314 |
| 3 | $n\text{-}C_{12}H_{25}NH_2$ | HO—, COOH, CONHC$_{12}$H$_{25}$ naphthalene | −50.2 | 310 |
| 4 | $n\text{-}C_{18}H_{37}NH_2$ | HO—, COOH, CONHC$_{18}$H$_{37}$ naphthalene | −51.0 | 310 |
| 5 | C$_6$H$_5$—NH$_2$ | HO—, COOH, CONH—C$_6$H$_5$ naphthalene | −29.1 | 302 |

TABLE 1-continued

| Ex. | amine/alcohol | naphthol derivative | tribofrictional charge (μC/g) | decomposition temp. (° C.) |
|---|---|---|---|---|
| 6 | 1-aminonaphthalene | 3-hydroxy-2-carboxy-6-(N-naphthyl)carbamoylnaphthalene | −13.0 | 290 |
| 7 | n-C$_{16}$H$_{33}$OH |  | −23.6 | 328 |

Formulation Examples

Examples of toner formula are shown below. In the following compositions, "part(S)" means "part(s) by weight". The formulation examples shown below are intended to illustrate the invention and not to be construed to limit the scope of the invention in any means.

Black Toner

Styrene-acrylic resin 100 parts, carbon black 6 parts and the compound of Example 1 2 parts are mixed uniformly with the ball mill, and then, the mixture is molten and kneaded with the dispersion kneader. The kneaded mixture is roughly crushed with the vibration mill and further pulverized with the jet mill to give the black toner.

Color Toner (Cyan)

Color toner (cyan) may be prepared in a manner similar to the black toner except for using polyester resin instead of styrene-acrylic resin and phthalocyanine blue instead of carbon black.

Color Toner (Yellow)

Color toner (yellow) may be prepared in a manner similar to the black toner except for using polyester resin instead of styrene-acrylic resin and hansa yellow instead of carbon black.

Color Toner (Magenta)

Color toner (magenta) may be prepared in a manner similar to the black toner except for using polyester resin instead of styrene-acrylic resin and rose bengal instead of carbon black.

INDUSTRIAL APPLICABILITY

The present invention provides a charge control agent for electrophotographic toners as well as an electro photographic novel naphthol derivative.

The invention claimed is:

1. An electrophotographic toner, comprising at least a binder resin, a colorant and a charge control agent consisting of the naphthol derivative represented by formula [I] or a salt thereof:

[I]

wherein Y is selected from the group consisting of an esterified carboxyl group and a group of —(CONH)n-X (wherein X is selected from the group consisting of an optionally branched and optionally substituted hydrocarbon group which may have an unsaturated bond, an optionally substituted aromatic group and a heterocyclic group having conjugated double bonds, and n is an integer of 1 or 2);

R is selected from the group consisting of a hydrogen atom, alkaline metal, optionally branched, optionally substituted C1 to C6 alkyl and acyl groups, and phenylalkyl group;

Q is selected from the group consisting of optionally branched C1 to C6 alkyl and alkoxy groups, halogen atom, nitro group, nitroso group, amino group and sulfo group; and m is an integer of 0 to 3.

2. The electrophotographic toner of claim 1, wherein the agent is negatively chargeable and the absolute amount of the charge is no less than +10.0 μC/g.

3. The electrophotographic toner of claim 1, which comprises 100 parts by weight of the binder resin, 1–20 parts by weight of the colorant and 0.1–10 parts by weight of the charge control agent.

4. The electrophotographic toner of claim 3, wherein Y is —(CONH)n-X, wherein n is 1 and X is a C8 to C18 alkyl group.

* * * * *